United States Patent [19]

Schulman et al.

[11] Patent Number: 4,938,215

[45] Date of Patent: * Jul. 3, 1990

[54] UMBILICAL CORD CLAMP AND CUTTERS

[75] Inventors: Norman M. Schulman, 8635 W. 3rd St. #665, Los Angeles, Calif. 90048; Donald Raible, Irvine, Calif.

[73] Assignee: Norman M. Schulman, Los Angeles, Calif.

[ * ] Notice: The portion of the term of this patent subsequent to Jan. 5, 2005 has been disclaimed.

[21] Appl. No.: 131,997

[22] Filed: Dec. 11, 1987

Related U.S. Application Data

[63] Continuation-in-part of Ser. No. 858,397, May 1, 1986, Pat. No. 4,716,886.

[51] Int. Cl.⁵ ............................................. A61B 17/08
[52] U.S. Cl. .................................... 606/120; 30/124; 606/174
[58] Field of Search ............... 128/305, 346, 326, 319, 128/320; 30/136, 124

[56] References Cited

U.S. PATENT DOCUMENTS

| | | | |
|---|---|---|---|
| 2,434,631 | 1/1948 | Brandenburg | 128/346 |
| 3,106,919 | 7/1962 | Churchville | 128/346 |
| 3,631,858 | 1/1972 | Ersek | 128/305 |
| 3,706,312 | 12/1972 | Melges | 128/305 |

Primary Examiner—Dalton L. Truluck
Assistant Examiner—Denise W. DeFranco
Attorney, Agent, or Firm—Spensley Horn Jubas & Lubitz

[57] ABSTRACT

A disposable double-clamp device for severing an umbilical cord while maintaining the severed ends thereof in a clamp. The clamps are held together in a side-by-side relation by a shear pin. A cutting blade is hingeably located between the abutting clamps, its forward cutting motion being impeded by said shear pin. After the device is brought into a clamped position, further pressure is exerted upon the blade, which breaks the shear pin and severs the umbilical cord.

33 Claims, 4 Drawing Sheets

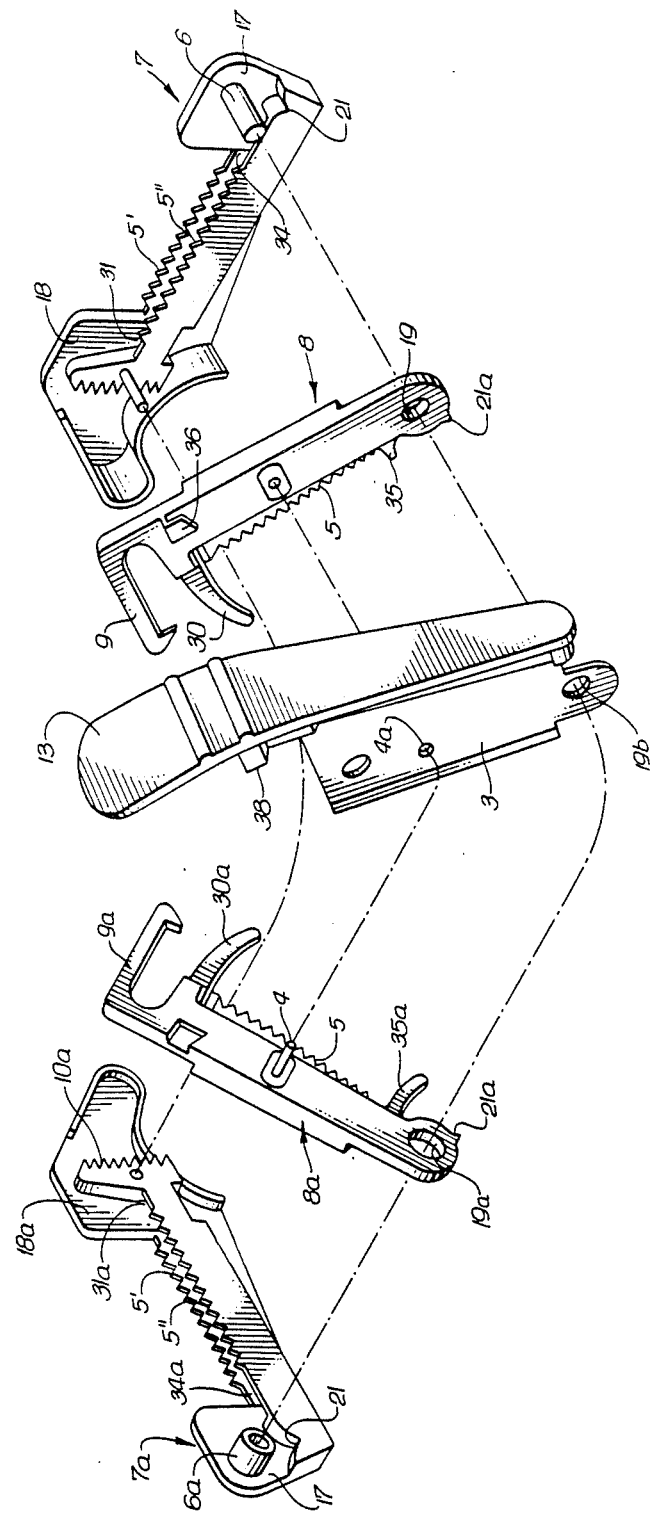

UMBILICAL CORD CLAMP AND CUTTERS

BACKGROUND OF THE INVENTION

This application is a continuation-in-part of copending application Ser. No. 858,397, now U.S. Pat. No. 4,716,886, entitled "Umbilical Cord Clamp and Cutters," filed May 1, 1986.

The present invention relates to a medical clamp and cutter of tubular bodies, particularly to a clamp and cutter for umbilical cords.

The umbilical cord is a tubular structure which connects a fetus with the placenta. The cord permits the exchange of waste products, oxygen and nutrients between a mother and her fetus Upon the baby's birth, a traditional method of severing the umbilical cord would involve the use of two clamps for clamping the cord at two points and a cutting blade for severing the cord between the two clamped points.

The above traditional method was time consuming, cumbersome and costly. As a result, various double clamp devices have been suggested for simultaneously clamping and cutting the umbilical cord. After severing the cord, however, these devices require an additional step to separate the placenta from the fetus while maintaining their respective clamped positions. For example, reference is made to the prior art devices disclosed in Whittaker, U.S. Pat. No. 2,524,337, Churchville, U.S. Pat. No. 3,106,919; Hurley, Jr., U.S. Pat. No. 3,323,208; and Mattler, U.S. Pat. No. 4,026,294. Each of these devices suffer from the disadvantage of requiring an additional step after cutting and clamping for separating the device. This additional step may be both time consuming and cumbersome, the disadvantages of which may be accentuated in an emergency situation when life and death may be determined by a matter of seconds U.S. patent application Ser. No. 858,397, "Umbilical Cord Clamp and Cutters," filed May 1, 1986, parent application hereto teaches a double-clamp device suitable for clamping and cutting umbilical cords. The invention of the present application is an improvement in the double-clamp device claimed in U.S. patent application Ser. No. 858,397, the teachings of which are hereby incorporated by reference.

An object of the present invention is to provide an improved double-clamp device which is able to simultaneously sever an umbilical cord while maintaining each severed end in a clamp.

Another object of the present invention is to provide an improved double-clamp device, which is inexpensive to produce, thereby permitting the device to be provided at a relatively low cost and effectively disposed of after each use.

SUMMARY OF THE INVENTION

In accordance with the present invention, these and other objectives are achieved in the following manner. The present invention's double-clamp device employs a pair of clamps in a side-by-side abutting relation, each clamp comprising a pair of arms, one upper and one lower, each pair of arms being connected by a hinge at one end and a latch at the other end for keeping the clamp in a clamped position. One of the arms of at least one of the clamps further comprises an anterior locking tongue and the other arm of the clamp comprises a slot. The anterior locking tongue and slot are adapted so that when the clamp is in a closed position the anterior locking tongue engages and passes through the slot. It is desirable that both clamps comprise one arm comprising an anterior locking tongue and one arm comprising a slot. One of the clamps, the cutting clamp, is connected to a cutting blade. The blade sits in a ready cutting position. The blade is hingeably sheathed between the two clamps, its cutting plane being along the plane separating the two clamps. The blade is adapted to hinge along the same axis as the arms of the clamps. Maintaining the clamps in a side-by-side relationship is a shear pin, which goes through a shear pin hole in the cutting blade and connects the upper arms of each clamp.

In accordance with the operation of the present invention, the double-clamp device is placed into position about the umbilical cord. After the device is so placed, the following operations are effected in substantially one motion. First, the device is squeezed together causing both clamps to close about the cord with the locking tongue engaging and passing through the slot. Further squeezing causes the blade, in the area of the shear pin hole, to be pressed downward against the shear pin, which breaks. Then, the cutting edge of the blade comes into contact with the umbilical cord and severs it.

As can be seen, the advantage of the present invention over the prior art is its ability to permit clamping, cutting, and separating of the cord in substantially one single motion, while maintaining clamps about both ends of the severed cord. Two examples of improvements in the present invention over related application Ser. No. 858,397 is the addition of the anterior locking tongue and slot and the hinging of the cutting blade between the two clamps.

BRIEF DESCRIPTION OF THE DRAWINGS

A detailed description of the invention will be made with reference to the accompanying drawings, wherein like numerals designate corresponding parts in the several figures.

FIG. 2 is an exploded view of the double-clamp device.

DESCRIPTION OF THE PREFERRED EMBODIMENT

Figure 1:
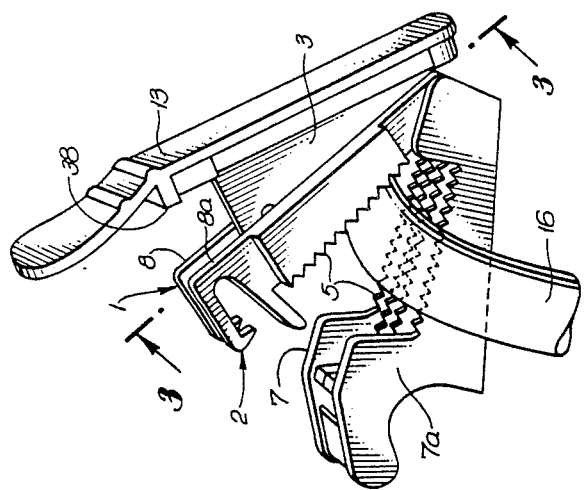
FIG. 1 is a perspective view of the improved double-clamp device of the present invention prior to cutting.

FIG. 1 shows the improved double-clamp device of the present invention. The double-clamp device consists of clamp 1 in a side-by-side abutting relation with clamp 2. Clamps 1 and 2 are joined together side-by-side by a single shear pin 4 joining the upper arms 8,8a as shown in FIG. 2. Other means for selectively joining clamps 1 and 2 together are within the scope of the present invention. For example, another shear pin, bridge, web or similar element could extend from and join lower arms 7,7a.

As seen in FIG. 2, clamps 1 and 2 are each comprised of a pair of elongated lower arms 7,7a and elongated upper arms 8,8a. Both pairs of upper and lower arms preferably have a series of serrations 5 either perpendicular to the length of the arms parallel or at an angle on their adjacent faces. When arms 7,7a and 8,8a are clamped together, their teeth mesh together for excellent gripping ability. In the illustrated embodiment of the present invention, each lower arm 7,7a has two series or serrations 5',5''. One series of serrations 5' is located proximate an outer surface of the clamp, the other series of serrations 5'' is located proximate an inner surface of the clamp. Serrations 5' are adapted to engage with the serrations on upper arm 8. Serrations 5'' are adapted to assist a cutting blade 3 in severing an umbilical cord.

Arms 7,7a and 8,8a are connected at one end by pivot pins 6,6a and barrel openings 19,19a, which together form a pair of pin-barrel hinges. Pivot pins 6,6a are each integrally connected to backwalls 17,17a of lower arms 7,7a. In addition, as seen in FIG. 2, pivot pin 6a is hollow so that pivot pin 6 slidingly fits into pivot pin 6a, thereby providing further stability to the two clamps while in a side-by-side position. However, pins 6,6a are designed so that they can be readily separated.

Figure 5:
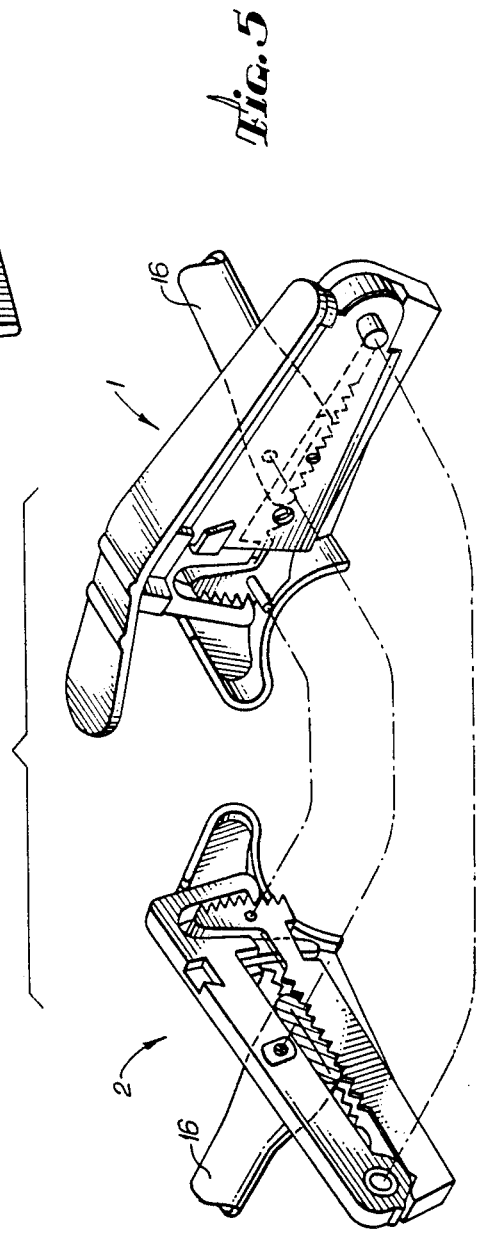
FIG. 5 is a perspective view of the improved double-clamp device after clamping, cutting, and separating.

In one improved embodiment, arms 7,7a each define a small detent 21 into which protrusion 21a on arms 8,8a extends. This is illustrated in FIGS. 2 and 5. Protrusion 21a and detent 21 are positioned such that the arms 8,8a are selectively retained in an open position forming an angle of about 40 to about 80 degrees with respect to arms 7,7a.

In FIG. 2, lower arms 7 and 7a each define an opening 34,34a into which a posterior locking tongue 35,35a, located on upper arms 8,8a extend when the clamps are in a clamped position. Openings 34,34a and posterior locking tongues 35,35a cooperate to stabilize clamps 1 and 2 against lateral movement. That is, against the possibility of the upper arm and lower arm of either clamp 1 or 2 shifting, laterally, with respect to each other.

Connected at the other end of arms 7,7a and 8,8a, as seen in FIG. 2, are latching means, 9,9a, and associated receiving means, 10,10a. Latching means 9,9a are integrally connected to upper arms 8,8a, and are preferably configured like hooks, the bent lips being flat and at acute angles. Receiving means 10,10a are preferably serrated, with rows of flat surfaced teeth, so that latching means 9,9a may matingly latch onto different levels of teeth. Receiving means 10,10a are each integrally connected to backwalls 18,18a of lower arms 7,7a.

In FIG. 2, upper arms 8 and 8a are shown as further comprising anterior locking tongues 30 and 30a. Lower arms 7 and 7a are shown as further comprising slots 31 and 31a. Anterior locking tongues 30 and 30a and slots 31 and 31a are operably located so that when arms 7 and 8, and 7a and 8a are respectively engaged and in a clamped and locked position anterior locking tongue 30 passes through slot 31 and anterior locking tongue 30a passes through slot 31a thus preventing lateral slippage of arms 7 and 8, and 7a and 8a relative to one another.

As shown in the Figures, cutting blade 3 is disposed in a slot formed between clamps 1 and 2 so that cutting takes place along the plane separating clamps 1 and 2. Cutting blade 3 is shown as being adapted to pivot along pivot pin 6a. Barrel opening 19b is designed to operably receive pivot pin 6a. As shown in FIG. 2, the end of cutting blade 3 opposite barrel opening 19b gradually tapers towards barrel opening 19b. Cutting blade 3 comprises shear pin hole 4a designed to receive shear pin 4 as previously described.

Figure 3:
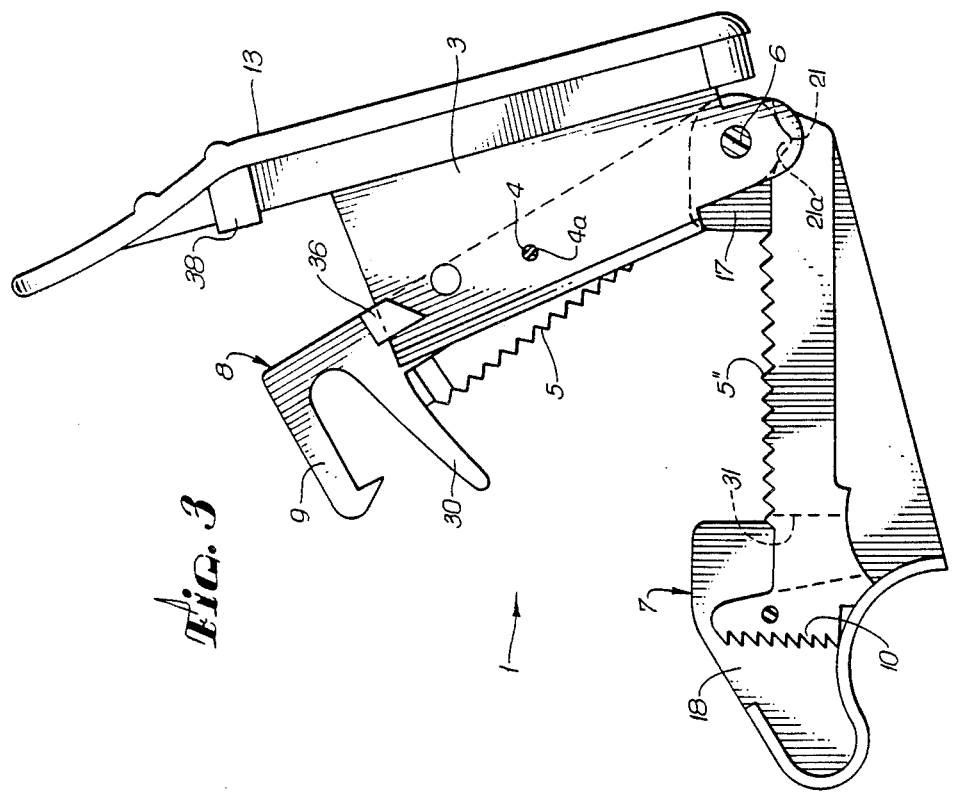
FIG. 3 is a perspective view of the improved double-clamp device taken along line 3—3 of FIG. 1.
Figure 4:
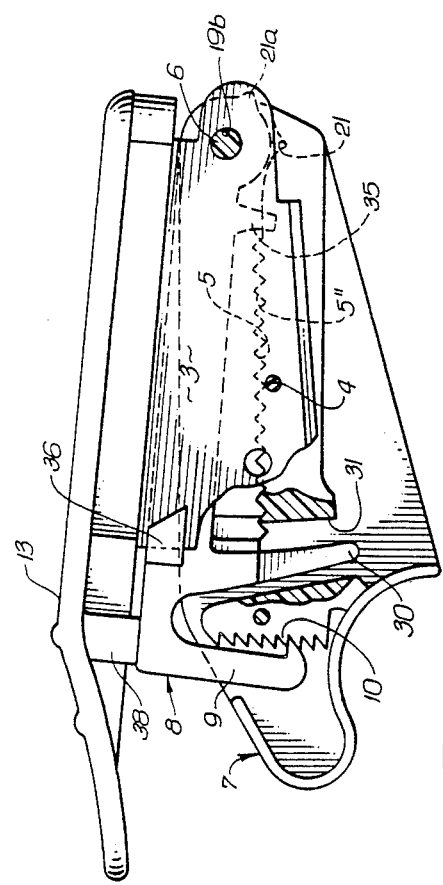
FIG. 4 is a perspective view of the section illustrated in FIG. 3 after clamping.

As evidenced by FIGS. 3–5, during its cutting action, blade 3 moves down along the plane separating clamps 1 and 2. The blade 3 is guided by blade guide 36 located on upper arm 7. Blade guide 36 guides blade 3 along the plane between clamps 1 and 2 and serves to retain the blade 3 on clamp 1 after clamps 1 and 2 have been separated. Pressure for cutting is enhanced by handle 13, atop of blade 3. Handle 13 provides a greater surface area for hand pressure. Integrally attached to handle 13 is contact bar 38. Contact bar 38 is adapted to contact upper arms 8,8a as cutting blade 3 is moved along the plane separating clamps 1 and 2. When contact bar 38 contacts upper arms 8,8a it serves to equalize the pressure asserted on each upper arm. In this manner, both clamps are brought into a fully clamped position during the clamping and cutting process.

Figure 6:
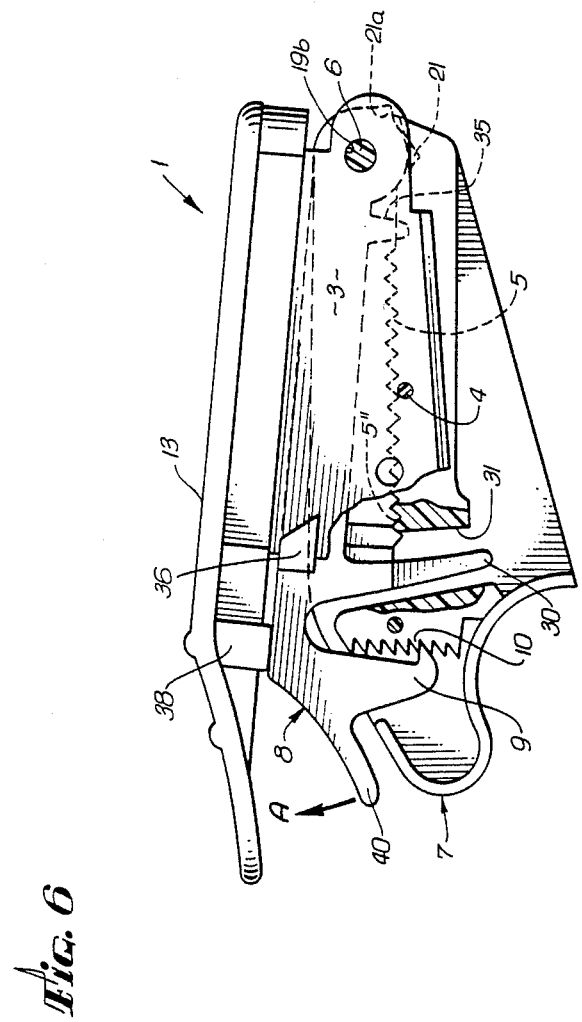
FIG. 6 is a second embodiment of one clamp of the double-clamp device.

In one embodiment of the present invention, at least one clamp comprises means for disengaging the latching means 9,9a from the receiving means 10, 10a. Any means capable of disengaging the latching means 9,9a from the receiving means 10,10a is suitable for use in the present invention. Exemplary of such means is disengaging means 40 illustrated in FIG. 6. Disengaging means 40 is adapted to move latching means 9 away from receiving means 10 thus allowing clamp 1 to be opened. When a force is applied to disengaging means 40 in a direction indicated by arrow A latching means 9 moves out of contact with receiving means 10.

The ability to open at least one clamp after severing the umbilical cord is useful in those situations where it is desired to reposition at least one clamp after the cutting and clamping operation is complete.

Clamps 1 and 2 are each preferably molded as unitary units from a nontoxic, sterilizable inexpensive plastic material. The plastic material should be sufficiently rigid so that the clamps easily engage into a secure clamped position. Other types of material for the clamps are within the scope of the present invention. The shear pin joining the two clamps may be molded as an integral part of upper clamp 9 (FIG. 2) or as a separate pin made of any rigid material that can be easily broken by the application of squeezing pressure from one's hand. The shear pin material, however, should withstand any lesser pressure to ensure clamp closure.

Cutting blade 3 is suitably formed from any sterilizable material capable of forming a cutting edge of sufficient sharpness and hardness to perform the cutting operation. Beneficially, cutting blade 3 is formed from a metal material, such as stainless steel. Additionally, cutting blade 3 may be formed in part from a plastic material and in part from a metal material.

The operation of the present invention will now be explained in greater detail.

FIG. 1 shows the double-clamp device just prior to clamping about umbilical cord 16. Once the device is in position, as indicated in FIGS. 1 and 3, it is ready for the nearly simultaneous clamping, cutting and separating of umbilical cord 16. As the arms 7 and 8, and 7a and 8a are closed together, the device is secured about the cord 16. As the arms close about cord 16, the latching and receiving means 9,9a and 10,10a engage. The cord 16 is now firmly held in place at two distinct locations; to wit: between arms 7 and 8 and 7a and 8a.

Further squeezing of the device causes cutting blade 3 to move downward, causing blade 3, in the area of shear pin hole 4a, to confront and break shear pin 4. As blade 3 continues to travel downward towards the end of the cut, it confronts and cuts umbilical cord 16. After cord 16 is completely severed, lateral pressure is applied to completely separate clamps 1 and 2. This pressure may be applied by the operator if necessary, or it may occur spontaneously due to the weight of the cord itself.

As seen in FIG. 5, each clamp maintains its clamped position about each end of the severed umbilical cord.

The above description of presently preferred embodiment of the invention was intended to illustrate by way of example the novel features that are believed to be characteristics of the present invention. It is to be expressly understood, however, that the specific embodiment is for the purpose of illustration and description only, and is not intended as a definition of the limits of the invention. Other embodiments of the invention are therefore included within the scope of this invention.

What is claimed is:

1. A device for the clamping and severing of a tubular body, each severed end thereof being retained in a clamp, the device comprising:
   a pair of clamps, each clamp comprising a pair of arms hingeably connected at one end and further having latching means for securing said pair of arms in a clamped position about said tubular body;
   breakable connecting means for selectively connecting and maintaining said pair of clamps in a side-by-side abutting relation; and
   a cutting blade connected between said clamps, for breaking said connecting means and severing said tubular body,
   at least one arm of each of said clamps and said cutting blade being pivotably connected to common pivot means, said pivot means forming a disengageable connection among said clamps and said cutting blade,
   whereby clamping and cutting of said tubular body is done substantially in a single motion.

2. The device as claimed in claim 1 wherein one arm of each clamp comprises a pin and the other arm of each clamp defines an opening adapted to hingeably receive said pin.

3. A device for the clamping and severing of a tubular body, each severed end thereof being retained in a clamp, the device comprising:
   a pair of clamps, each clamp comprising a pair of arms hingeably connected at one end and further having latching means for securing said pair of arms in a clamped position about said tubular body;
   breakable connecting means for selectively connecting and maintaining said pair of clamps in a side-by-side abutting relation; and
   a cutting blade hingeably connected between said clamps, for breaking said connecting means and severing said tubular body, whereby clamping and cutting of said tubular body is done substantially in a single motion,
   wherein one arm of each clamp comprises a pin and the other arm of each clamp defines an opening adapted to hingeably receive said pin, and wherein one of said pins is hollow and adapted to slidingly receive the other pin.

4. The device as claimed in claim 3 wherein the cutting blade defines an opening adapted to hingeably receive at least one of said pins.

5. The device as claimed in claim 1 wherein one of said clamps further comprises a blade guide for guiding the blade between said clamps.

6. The device as claimed in claim 1 wherein at least one of the clamps comprises a locking tongue located on one of the arms of said clamp and a slot located on the other arm of said clamp, said slot being adapted to receive the locking tongue when said clamp is in a clamped position.

7. The device as claimed in claim 1 wherein the blade further comprises a handle having integrally attached thereto a contact bar adapted to contact one arm of each clamp during the cutting and clamping process.

8. The device as claimed in claim 1 further comprising means for disengaging the latching means.

9. The device as claimed in claim 1 wherein said latching means secures said pair of arms in a clamped position prior to severing the tubular body.

10. A double-clamp device for clamping and severing an umbilical cord while retaining each severed end thereof in a clamp, the device comprising:
    a pair of clamps, each clamp comprising a pair of elongated arms hingeably connected at one end, one of said clamps including a first locking tongue located on one of the arms of said clamp and a first slot located on the other arm of said clamp, said first slot being adapted to receive said first locking tongue when said clamp is in a clamped position, and further wherein said clamps have latching means for securing said pair of arms in a clamped position about said cord;
    breakable connecting means for selectively maintaining said pair of clamps in a side-by-side abutting relation; and
    a cutting blade connected between said clamps, for severing said umbilical cord and breaking said connecting means, at least one arm of each of said clamps and said cutting blade being pivotally connected to common pivot means, said pivot means forming a disengageable connection among said clamps and said cutting blade.

11. The device as claimed in claim 10 wherein both of said clamps include a first locking tongue and first slot.

12. The device as claimed in claim 10 where in the first locking tongue and slot are located near the end of the clamp remote from the end at which the arms are hingeably connected.

13. A double-clamp device for clamping and severing an umbilical cord while retaining each severed end thereof in a clamp, the device comprising:
    a pair of clamps, each clamp comprising a pair of elongated arms hingeably connected at on- end, one of said clamps including a first locking tongue located on one of the arms of said clamp and a first slot located on the other arm of said clamp, said first slot being adapted to receive said first locking tongue when said clamp is in a clamped position, and further wherein said clamps have latching means for securing said pair of arms in a clamped position about said cord;
    breakable connecting means for selectively maintaining said pair of clamps in a side-by-side abutting relation; and
    a cutting blade hingeably connected between said clamps, for severing said umbilical cord and breaking said connecting means, wherein at least one of the clamps comprises a second locking tongue located on one of the arms of said clamp and a seconnd slot located on the other arm of said claim, said second slot being adapted to receive the second locking tongue when said clamp is in a clamped position.

14. The device as claimed in claim 13 wherein both of said clamps include a second locking tongue and second slot.

15. The device as claimed in claim 13 wherein said second locking tongue and slot are located near the end of the clamp at which the arms are hingeably connected.

16. The device as claimed in claim 10 wherein one of said clamps further comprises a blade guide for guiding the blade between said clamps.

17. The device as claimed in claim 10 wherein the blade further comprises a handle having integrally attached thereto a contact bar adapted to contact one arm of each clamp during the cutting and clamping process.

18. The device as claimed in claim 10 wherein said latching means secures said pair of arms in a clamped position prior to severing the tubular body.

19. The device as claimed in claim 10 further comprising means for disengaging the latching means for securing said arms in a clamped position.

20. A device for the clamping and severing of a tubular body, each severed and thereof being retained in a clamp, the device comprising:
  a pair of clamps, each clamp comprising an upper and a lower arm hingeably connected about a common axis at their posterior ends, both of said clamps comprising locking tongues located near the anterior end of the upper arm of each of said clamps and slots located near the anterior end of the lower arm of each of said clamps, the slots being adapted to receive the locking tongues when the clamps are in a clamped position about said tubular body;
  connecting means for selectively maintaining said pair of clamps in a side-by-side abutting relation; and
  a cutting blade connected about the common axis and located between the clamps, for severing the tubular body, at least one arm of each of said clamps and said cutting blade being pivotably connected to common pivot means, said pivot means forming a disengageable connection among said clamps and said cutting blade.

21. A device for the clamping and severing of a tubular body, each severed end thereof being retained in a clamp, the device comprising:
  a pair of clamps, each clamp comprising an upper and a lower arm hingeably connected about a common axis at their posterior ends, both of said clamps comprising locking tongues located near the anterior end of the upper arm of each of said clamps and slots located near the anterior end of the lower arm of each of said clamps, the slots being adapted to receive the locking tongues when the clamps are in a clamped position about said tubular body;
  connecting means for selectively maintaining said pair of clamps in a side-by-side abutting relation; and
  a cutting blade hingeably connected about the common axis and located between the clamps for severing the tubular body, wherein both of said clamps further comprise locking tongues located near the posterior end of the upper arm of each of said clamps and slots located near the posterior end of the lower arm of each of said clamps the slots being adapted to receive the locking tongues when the clamps are in a clamped position about said tubular body.

22. The device as claimed in claim 20 further comprising latching means located on one and of each of said clamps and receiving means located on the other arm of each of said clamps said latching means being adapted to matingly latch onto said receiving means to secure each pair of arms in a clamped position.

23. The device as claimed in claim 22 wherein the latching means are integrally connected to the upper arms and are shaped like a hook.

24. The device as claimed in claim 23 wherein the receiving means are integrally connected to the lower arms and comprise rows of flat surfaced teeth adapted to allow the latching means to matingly latch onto different rows of teeth.

25. The device as claimed in claim 20 wherein the lower arm of each clamp comprises a pin and the upper arm of each clamp defines an opening adapted to hingeably receive said pin.

26. A device for the clamping and severing of a tubular body, each severed end thereof being retained in a clamp, the device comprising:
  a pair of clamps, each clamp comprising an upper and a lower arm hingeably connection about a common axis at their posterior ends, both of said clamps comprising locking tongues located near the anterior end of the upper arm of each of said clamps and slots located near the anterior end of the lower arm of each of said clamps, the slots being adapted to receive the locking tongues when the clamps are in a clamped position about said tubular body, the lower arm of each clamp comprising a pin and the upper arm of each clamp defining an opening adapted to hingeably receive said pin;
  connecting means for selectively maintaining said pair of clamps in a side-by-side abutting relation; and
  a cutting blade hingeably connected about the common axis and located between the clamps, for severing the tubular body, wherein one of said pins is hollow and adapted to slidingly receive the other pin.

27. The device as claimed in claim 20 wherein the blade further comprises a handle having integrally attached thereto a contact bar adapted to contact the anterior end of the upper arm of each clamp during the cutting and clamping process.

28. The device as claimed in claim 20 wherein the upper arm of one of the clamps further comprises a blade guide adapted to guide the blade between the clamps and to retain the blade on said clamp after cutting and clamping.

29. A device for the clamping and severing of a tubular body, each severed end thereof being retainer in a clamp, the device comprising:
  a pair of clamps, each clamp comprising an upper and a lower arm, each lower arm comprising a pin and each upper arm defining an opening adapted to hingeably receive said pin thus hingeably connecting the arms about a common axis at their posterior ends, both of said clamps comprising locking tongues located near the anterior end of the upper arm of each of said clamps and slots located near the anterior end of the lower arm of said clamps the slots being adapted to receive the locking tongues when the clamps are in a clamped position about said tubular body;

latching means integrally connected to the anterior end of the upper arm of each of said clamps, said latching means being shaped like a hook;

receiving means integrally connected to the anterior end of each of the lower arms of said clamps, said receiving means comprising rows of flat surface teeth adapted to allow the latching means to matingly latch onto different rows of teeth;

connecting means for selectively maintaining said pair of clamps in a side-by-side abutting relation; and a cutting blade hingeably connected about the common axis and located between the clamps, for severing the tubular body, at least the upper arm of each of said clamps and said cutting blade being pivotably connected to common pivot means, said pivot means forming a disengageable connection among said clamps and said cutting blade.

30. A device for the clamping and severing of a tubular body, each severed end thereof being retained in a clamp, the device comprising:

a pair of clamps, each clamp comprising an upper and a lower arm, each lower arm comprising a pin and each upper arm defining an opening adapted to hingeably receive said pin thus hingeably connecting the arms about a common axis at their posterior means, both of said clamps comprising locking tongues located near the anterior end of the upper arm of each of said clamps and slots located near the anterior end of the lower arm of each of said clamps, the slots being adapted to receive the locking tongues when the clamps are in a clamped position about said tubular body;

latching means integrally connected to the anterior end of the upper arm of each of said clamps, said latching means being shaped like a hook;

receiving means integrally connected to the anterior end of each of the lower arms of said clamps, said receiving means comprising rows of flat surface teeth adapted to allow the latching means to matingly latch onto different rows of teeth;

connecting means for selectively maintaining said pair of clamps in a side-by-side abutting relation; and a cutting blade hingeably connected about the common axis and located between the clamps, for severing the tubular body, wherein the cutting blade defines an opening adapted to hingeably receive one of the pins.

31. A device for the clamping and severing of a tubular body, each severed end thereof being retained in a clamp, the device comprising:

a pair of clamps, each clamp comprising an upper and a lower arm, each lower arm comprising a pin and each upper arm defining an opening adapted to hingeably receive said pin thus hingeably connecting the arms about a common axis at their posterior ends, both of said clamps comprising locking tongues located near the anterior end of the upper arm of each of said clamps and slots located near the anterior end of the lower arm of each of said clamps, the slots being adapted to receive the locking tongues when the clamps are in a clamped position about said tubular body;

latching means integrally connected to the anterior end of the upper arm of each of said clamps, said latching means being shaped like a hook;

receiving means integrally connected to the anterior end of each of the lower arms of said clamps, said receiving means comprising rows of flat surface teeth adapted to allow the latching means to matingly latch onto different rows of teeth;

connecting means for selectively maintaining said pair of clamps in a side-by-side abutting relation; and a cutting blade hingeably connected about the common axis and located between the clamps, for severing the tubular body, wherein both of said clamps further comprise locking tongues located near the posterior end of the upper arm of each of said clamps and slots located near the posterior end of the lower arm of each of said clamps, the slots being adapted to receive the locking tongue when the clamps are in a clamped position about said tubular body.

32. The device as claimed in claim 29 wherein the blade further comprises a handle having integrally attached thereto a contact bar adapted to contact the anterior end of the upper arm of each clamp during the cutting and clamping process.

33. The device as claimed in claim 29 wherein the upper arm of one of the clamps further comprises a blade guide adapted to guide the blade between the clamps and to retain the blade on said clamp after cutting and clamping.

* * * * *